(12) United States Patent
Kulkarni

(10) Patent No.: US 7,342,121 B1
(45) Date of Patent: Mar. 11, 2008

(54) METHOD OF PRODUCING HIGH DENSITY TOCOPHEROL ACID SUCCINATE

(75) Inventor: Madhu V. Kulkarni, Bourbonnais, IL (US)

(73) Assignee: Cognis Corporation, Ambler, PA (US)

( * ) Notice: Subject to any disclaimer, the term of this patent is extended or adjusted under 35 U.S.C. 154(b) by 79 days.

(21) Appl. No.: 11/342,255

(22) Filed: Jan. 27, 2006

Related U.S. Application Data

(63) Continuation of application No. 10/933,820, filed on Sep. 3, 2004, now abandoned, which is a continuation of application No. 10/361,789, filed on Feb. 10, 2003, now abandoned, which is a continuation of application No. 10/214,030, filed on Aug. 7, 2002, now abandoned, which is a continuation of application No. 10/037,150, filed on Oct. 19, 2001, now abandoned, which is a continuation of application No. 09/867,319, filed on May 29, 2001, now abandoned, which is a continuation of application No. 09/728,637, filed on Dec. 1, 2000, now abandoned, which is a continuation of application No. 09/421,820, filed on Oct. 20, 1999, now abandoned, which is a continuation of application No. 09/299,686, filed on Apr. 26, 1999, now abandoned, which is a continuation of application No. 08/926,628, filed on Sep. 10, 1997, now abandoned, which is a continuation of application No. 08/706, 632, filed on Sep. 6, 1996, now abandoned, which is a continuation-in-part of application No. 08/577,360, filed on Dec. 22, 1995, now abandoned, which is a continuation-in-part of application No. 08/380,462, filed on Jan. 27, 1995, now abandoned.

(51) Int. Cl.
*C07D 311/72* (2006.01)
(52) U.S. Cl. ...................................... 549/410
(58) Field of Classification Search ................ 549/410
See application file for complete search history.

(56) References Cited

U.S. PATENT DOCUMENTS

| | | | | |
|---|---|---|---|---|
| 4,870,196 A | * | 9/1989 | Thorengaard | 549/410 |
| 5,686,632 A | * | 11/1997 | Walsh | 549/410 |
| 6,130,343 A | * | 10/2000 | Hunsicker et al. | 549/410 |

\* cited by examiner

*Primary Examiner*—Patricia L Morris
(74) *Attorney, Agent, or Firm*—John F. Daniels

(57) ABSTRACT

A process is described for making high density tocopherol succinate powder. In this process, a solution of tocopherol succinate is prepared in hexane. The hexane is removed under heat and pressure. The resulting powder is then mixed with hexane yielding larger particles and a denser product. In the process, an atmosphere enriched in nitrogen is maintained over said tocopherol powder during said process.

8 Claims, No Drawings

METHOD OF PRODUCING HIGH DENSITY TOCOPHEROL ACID SUCCINATE

CROSS-REFERENCE TO RELATED APPLICATIONS

This application claims priority under 35 U.S.C. §120, and is a continuation of U.S. patent application Ser. No. 10/933,820, filed on Sep. 3, 2004 now abandoned, which is a continuation of U.S. patent application Ser. No. 10/361, 789, filed on Feb. 10, 2003 (now abandoned), which is a continuation of U.S. patent application Ser. No. 10/214,030, filed Aug. 7, 2002 (now abandoned), which is a continuation of U.S. patent application Ser. No. 10/037,150, filed Oct. 19, 2001 (now abandoned), which is a continuation of U.S. patent application Ser. No. 09/867,319, filed May 29, 2001 (now abandoned), which is a continuation of U.S. patent application Ser. No. 09/728,637, filed Dec. 1, 2000 (now abandoned), which is a continuation of U.S. patent application Ser. No. 09/421,820, filed Oct. 20, 1999 (now abandoned), which is a continuation of U.S. patent application Ser. No. 09/299,686, filed Apr. 26, 1999 (now abandoned), which is a continuation of U.S. patent application Ser. No. 08/926,628, filed Sep. 10, 1997 (now abandoned), which is a continuation of U.S. patent application Ser. No. 08/706, 632, filed Sep. 6, 1996 (now abandoned), which is a continuation-in-part of U.S. patent application Ser. No. 08/577, 360, filed Dec. 22, 1995 (now abandoned), which is a continuation-in-part of U.S. patent application Ser. No. 08/380,462, filed Jan. 27, 1995 (now abandoned), the entire contents of each of which are hereby incorporated by reference.

FIELD OF THE INVENTION

The present invention relates to a method and more particularly, it relates to a method of producing high density alpha-tocopherol acid succinate powder having the following structural formula (I):

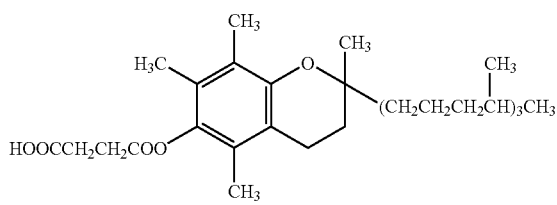

BACKGROUND OF THE INVENTION

Vitamin E designates a group of naturally occurring compounds known as tocopherols which comprise, for example, alpha-tocopherol, beta-tocopherol, gamma-tocopherol and delta-tocopherol. These compounds are found, for example, in vegetation, seeds, cereals, nuts and the like.

Vitamin E is known as an membranous antioxidant. It plays a part in the membranous parts of cells. Thus, it interdigitates with phospholipids, cholesterol and triglycerides, the three main structural elements of membranes. Because Vitamin E acts as an antioxidant, it reacts at the cell sites with the destructive compounds known as free radicals. Vitamin E converts these free radicals into a less harmful form. In addition, Vitamin E is said to have an antisterility function. Therapeutically, it is indicated for a variety of clinical conditions, such as prevention of abortion, improve fertility, in addition to its nutritional values administered in the form of dietary supplements. Of the tocopherols, d-alpha-tocopherols has the greatest biological activity.

DESCRIPTION OF PRIOR ART

Tocopherol acid succinate (I) is also known as Vitamin E acid succinate. The formula is:

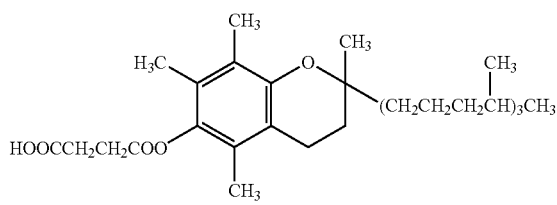

Briefly, Compound I can be prepared by treating alpha-tocopherol with succinic anhydride. The resulting compound is recovered in the form of needles following crystallization from petroleum ether. It has a melting point of 76-77°. For a more detailed description, please see: Demone et al., Helv. Chim. Acta 22, 65 (1939); McArthur, Watson, Can. Chem. Process Inds. 23, 350 (1939); Baxter, et al., J. Am. Chem. Soc. 65, 918 (1943), and U.S. Pat. No. 2,680, 749 (Cawley et al.).

SUMMARY OF THE INVENTION

We have now found a novel method of producing high density compound (I) in powder form. This method comprises first, forming a solution of tocopherol succinate in hexane. The hexane in succinate solution is removed under heat and vacuum. Residual traces of hexane are then removed under low pressure yielding tocopherol succinate powder which is mixed together. A controlled amount of hexane is sprayed on top of the mixed powder under low pressure and agitation. The hexane binds the particles which evaporates quickly yielding a bigger and denser tocopherol succinate. The improvement of this invention comprises maintaining an atmosphere enriched in nitrogen over said tocopherol powder during said process.

DESCRIPTION OF THE INVENTION

The present invention relates to a method and more particularly, it relates to a method of producing high density alpha-tocopherol acid succinate having the above described structural formula (I) in powder form.

According to the present invention, tocopherol succinate is first dissolved in hexane to give an approximate solid content from about 25% to about 55% by weight and preferably at about 40%. The resulting solution is transferred to a suitable evaporating vessel equipped with heating and vacuum system. The hexane is removed under suitable heat and vacuum. When enough hexane has been evaporated, the succinate solution goes through a stage of super saturation and then a sudden crystallization. A large amount heat of crystallization is released during this operation. This heat helps to evaporate the remaining amount of hexane in a sudden burst. The vacuum keeps the temperature of the batch sufficiently low to keep the succinate in solid state. Then, dry nitrogen gas, preferably at a purity of at least about 95% by weight is introduced into the vessel and the atmosphere within the vessel is swept with dry nitrogen gas until the partial pressure of nitrogen gas within the atmosphere is at least 95% of the total gas pressure within the vessel. Thereafter, the product is held under about 2 to 5 mm of pressure to remove the residual traces of hexane.

The succinate powders thus obtained are combined to form larger agglomerates. A controlled amount of hexane is sprayed on the top of the mixed powder under low pressure and agitation. The hexane binds the agglomerates together. The hexane which stays on the surface of the agglomerates quickly evaporates at room temperature yielding a high density bigger size tocopherol succinate powder. In preferred embodiments of this invention, the resulting product is agglomerated in accordance with PCT Application No. US96/05322, filed Apr. 23, 1996, the disclosure of which is incorporated herein by reference. That agglomeration process comprises contacting a tocopheryl succinate powder with a solution of a pharmaceutically acceptable binder, said tocopheryl succinate being maintained in a fluidized bed during said contacting by passage of a fluidizing gas through said bed. The solvent is then evaporated from said contacted tocopheryl succinate in said fluidized bed. The temperature of said fluidizing gas when introduced into said bed is sufficiently low, e.g. no higher than about 30° C., such that the bed of tocopheryl succinate remains in a fluidized state during said contacting and said evaporating. In order to further illustrate the practice of this invention, the following Example is included.

EXAMPLE 1

A sufficient amount of tocopherol succinate is dissolved in hexane to yield about a 40% by weight solution. The solution is charged to a Groen kettle equipped with a heating and vacuum system. A controlled amount of heat and vacuum is applied to the kettle to remove the hexane. When enough hexane has been evaporated, the succinate solution goes through a stage of super saturation and then a sudden crystallization. A large amount of heat of crystallization is released during this operation. This heat helps to evaporate the remaining amount of hexane. In the meantime, the vacuum system helps to keep the temperature sufficiently low to maintain the succinate in solid state. Dry nitrogen gas at a purity of about 99% is introduced into the vessel and gas is vented from the vessel until the partial pressure of the nitrogen gas is at least 95% of the total pressure. Finally, a vacuum is applied to the content of the vessel and the powder is held under approximately 2 to 5 mm of pressure to remove traces of hexane. The succinate powders thus obtained, are mixed using simple blending procedures forming agglomerates. A nitrogen atmosphere is again established within the vessel and a controlled amount of hexane is sprayed on top of the agglomerates at a low pressure with gentle agitation. The hexane binds the agglomerates together. The hexane on the surface quickly evaporates yielding the desired tocopherol succinate in the form of a denser and larger particle.

Comparative Example 1

A sufficient amount of tocopherol succinate is dissolved in hexane to yield about a 40% by weight solution. The solution is charged to a Groen kettle equipped with a heating and vacuum system. A controlled amount of heat and vacuum is applied to the kettle to remove the hexane. When enough hexane has been evaporated, the succinate solution goes through a stage of super saturation and then a sudden crystallization. A large amount of heat of crystallization is released during this operation. This heat helps to evaporate the remaining amount of hexane. In the meantime, the vacuum system helps to keep the temperature sufficiently low to maintain the succinate in solid state. Finally, the powder is held under approximately 2 to 5 mm of pressure to remove traces of hexane. The succinate powders thus obtained, are mixed using simple blending procedures forming agglomerates. A controlled amount of hexane is sprayed on top of the agglomerates at a low pressure with gentle agitation. The hexane binds the agglomerates together. The hexane on the surface quickly evaporates yielding the desired tocopherol succinate in the form of a denser and larger particle.

What is claimed is:

1. In a process for making high density tocopherol succinate powder by the steps of:
   a) forming a solution of tocopherol succinate in hexane;
   b) applying heat and vacuum to remove hexane and precipitate a powder tocopherol succinate product;
   c) holding the product under a low pressure to remove residual hexane to provide a tocopherol succinate powder with a reduced hexane content and agitating the tocopherol succinate powder to form larger particles of the powder; and
   d) evaporating the hexane, the improvement which comprises: maintaining an atmosphere enriched in nitrogen over said tocopherol succinate powder during said process.

2. The process of claim 1 wherein the solution of tocopherol succinate in hexane contains about 25% to about 55% by weight of tocopherol succinate.

3. The process of claim 2 wherein the solution contains about 40% by weight of tocopherol.

4. The process of claim 1 wherein in step c) the low pressure is about 2 to 5 mm of pressure.

5. The process of claim 1 wherein steps c) and d) are carried out in a fluidized bed.

6. The process of claim 5 wherein a temperature of a fluidizing gas is not higher than about 30° C.

7. The process of claim 1 wherein the atmosphere enriched in nitrogen comprises at least about 95% nitrogen based on the total pressure.

8. The process of claim 2 wherein the tocopherol succinate powder is mixed before spraying hexane on the agitated powder.

\* \* \* \* \*